(12) United States Patent
Braude

(10) Patent No.: US 6,716,879 B2
(45) Date of Patent: Apr. 6, 2004

(54) METHODS FOR ANTI-TUMOR THERAPY

(75) Inventor: Irwin Braude, Seattle, WA (US)

(73) Assignee: Compass Pharmaceuticals, LLC, New York, NY (US)

(*) Notice: Subject to any disclaimer, the term of this patent is extended or adjusted under 35 U.S.C. 154(b) by 0 days.

(21) Appl. No.: 09/941,876

(22) Filed: Aug. 29, 2001

(65) Prior Publication Data

US 2002/0082243 A1 Jun. 27, 2002

Related U.S. Application Data

(60) Provisional application No. 60/229,181, filed on Aug. 30, 2000.

(51) Int. Cl.7 .............................................. A61K 31/18
(52) U.S. Cl. ..................... 514/602; 514/603; 514/604
(58) Field of Search ................................ 514/602, 603, 514/604

(56) References Cited

U.S. PATENT DOCUMENTS

| | | | |
|---|---|---|---|
| 5,658,565 A | | 8/1997 | Billiar et al. |
| 5,919,682 A | | 7/1999 | Masters et al. |
| 6,335,334 B1 | * | 1/2002 | Schindler et al. .......... 514/231.5 |
| 2002/0061887 A1 | | 5/2002 | Schindler et al. |

FOREIGN PATENT DOCUMENTS

| | | |
|---|---|---|
| DE | 3523705 | 1/1997 |
| DE | 198 30 430 | 1/2000 |
| DE | 198 30 431 | 1/2000 |
| EP | A 216 028 | 4/1987 |
| EP | A 347 168 | 12/1989 |
| EP | A 420-805 A3 | 10/1991 |
| EP | A 420-805 A2 | 10/1999 |
| RU | 79282 | 7/1982 |
| SU | 1685936 | 10/1991 |
| SU | 1687586 | 10/1991 |
| SU | 1754712 | 8/1992 |
| SU | 1794941 | 2/1993 |
| SU | 1796617 | 2/1993 |
| WO | WO 96/04311 | 2/1996 |
| WO | WO 98/02170 | 1/1998 |
| WO | WO 00/02850 | 1/2000 |
| WO | WO 00/02851 | 1/2000 |
| WO | WO 00/78145 | 12/2000 |

OTHER PUBLICATIONS

Horowitz, et al., (1988), Journal of Clinical Oncology, vol. 6 No. 2, pp. 308–314.

Bailar, et al., (1997), N. Engl. J. Med., vol. 336, pp. 1569–1574.

* cited by examiner

*Primary Examiner*—Rebecca Cook
(74) *Attorney, Agent, or Firm*—McDonnell Boehnen Hulbert & Berghoff

(57) ABSTRACT

Disclosed and claimed is a method for treating tumors using sulfonylamino-substituted N-aryl- or heteroarylcarboxamide derivatives.

49 Claims, No Drawings

METHODS FOR ANTI-TUMOR THERAPY

This application claims benefit of No. 60/229,181 filed Aug. 30, 2000.

BACKGROUND OF THE INVENTION

Approximately twenty percent of deaths from all causes in the United States are cancer-related. Although chemotherapy is a principal means of cancer treatment, the rate at which effective new drugs have become available for use in cancer chemotherapy has not increased (Horowitz et al., Journal of Clinical Oncology, Vol. 6, No. 2, pp. 308–314 (1988)). Despite many years of promising new therapies, cancer remains a major cause of morbidity and mortality (Bailar et al., N. Engl. J. Med. 336:1569–1574, 1997). Accordingly, there is a substantial need for new drugs that are effective in inhibiting the growth of tumors.

The compounds of the general class sulfonylamino carboxylic acid N-arylamides are known in the art as useful agents for soluble guanylate cyclase activation (Schindler, et al., WO 00/02850). Several other pharmacological uses have been described including, for example, anti-parasitic, antimicrobial, and fungicidal effects (EP-A-420 805 and Chemical Abstracts 122, 136 749; 120, 560; 119, 116 978; 116, 228 237; 116, 207 806; 115, 158 666, and 106, 152 850), an anthelminitic effect (DE-A-35 23 705), psychotropic effects (Chemical Abstracts 104, 33 896), and use in the treatment of atherosclerosis or arthritis (EP-A-347 168). The use of these compounds for anti-tumor treatment has not been disclosed or suggested.

SUMMARY OF THE INVENTION

The present invention is based on the entirely unexpected finding that sulfonylamino-substituted N-aryl- or heteroarylcarboxamide derivatives are an effective class of anti-tumor agent. In one aspect, the present invention provides novel methods for treating tumors that involve administering an effective amount of sulfonylamino-substituted N-aryl- or heteroarylcarboxamide derivatives, or pharmaceutically acceptable salts, esters, amides, or prodrugs thereof, to a patient in need of treatment. In a preferred embodiment, the compounds administered in the method of the present invention are N-phenyl{2-[(phenylsulfonyl)amino]phenyl}carboxamide derivatives. In an even more preferred embodiment, the compounds are {5-substituted-2-[(phenylsulfonyl)amino]phenyl}-N-benzamide derivatives.

In further aspects, the present invention provides a pharmaceutical composition comprising an effective amount for treating tumors of a compound according to the general formula or specific compound hereinafter disclosed, or a pharmaceutical salt thereof, in a suitable carrier. In yet a further aspect, the present invention discloses articles of manufacture comprising packaging material and the above pharmaceutical compositions.

DETAILED DESCRIPTION OF THE INVENTION

The instant invention discloses the use of sulfonylamino-substituted N-aryl- or heteroarylcarboxamides, and their pharmaceutically acceptable salts, esters, amides, and prodrugs thereof as anti-tumor agents.

The present compounds, or pharmaceutically acceptable salts, esters, amides, or prodrugs thereof, are useful in treating tumors from any tissue type. Examples of specific tumor types that the compounds may be used to treat include, but are not limited to, sarcomas, carcinomas, and mesotheliomas.

As used herein the term "mesothelioma" is used to refer to a neoplasm derived from the cells lining the pleura, pericardium, or peritoneum, including but not limited to lung mesotheliomas.

As used herein the term "sarcoma" refers to tumors of mesenchymal origin, including but not limited to stromal cell sarcomas, leiomyosarcomas, malignant fibrous histiocytoma, Ewing sarcoma, fibrosarcomas, chondrosarcomas, osteosarcomas, liposarcomas, rhabdomyo-sarcomas, hemangiocytomas, and myxosarcomas.

As used herein the term "carcinoma" is used to refer to a neoplasm derived from epithelial cells.

As used herein the term "ovarian carcinoma" refers to neoplasms derived from ovarian cells of epithelial origin, including but not limited to ovarian papillary serous cystadenoma, ovarian endometroid carcinoma, mucinous, clear cell and Brenner epithelial tumors.

In one embodiment, the sulfonylamino-substituted N-aryl- or heteroarylcarboxamides compounds comprise the general formula I, in all their stereoisomeric forms and mixtures thereof, in all proportions (see Schindler, et al., WO 00/02850).

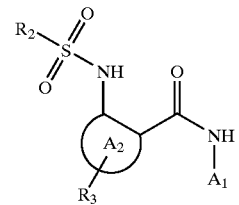

I wherein
$A_1$ is aryl or heteroaryl, each of which may be optionally substituted with one, two or three groups independently selected from halogen, aryl, —$CF_3$, —$NO_2$, —OH, —O—($C_1$-$C_7$)-alkyl, —O—($C_2$-$C_4$)-alkyl-O—($C_1$-$C_7$)-alkyl, —O-aryl, ($C_1$-$C_2$)-alkylenedioxy, —$NR_5R_6$, —CN, —CO—$NR_5R_6$, —COOH, —CO—O—($C_1$-$C_5$)-alkyl, heterocyclyl, —CHO, —CO—($C_1$-$C_{10}$)-alkyl, —CO-aryl, —CO-heteroaryl, or ($C_1$-$C_{10}$)-alkyl, ($C_3$-$C_{10}$)-cycloalkyl, ($C_1$-$C_{10}$)-alkenyl or ($C_1$-$C_{10}$)-alkynyl, each of which is optionally substituted with up to five groups independently selected from halogen, —OH, aryl, heteroaryl, —O—($C_1$-$C_{10}$)-alkyl, —O—($C_1$-$C_7$)-alkyl-$R_7$, —O-aryl, —O-heteroaryl, —SH, —S—($C_1$-$C_{10}$)-alkyl, —S—($C_1$-$C_7$)-alkyl-$R_7$, —S-aryl, —S-heteroaryl, —P(O)(O—($C_1$-$C_5$)-alkyl)$_2$, —P(O)(OH)$_2$, —CN, —$NR_8R_9$, —CO—$NH_2$, —CO—NH—($C_1$-$C_3$)-alkyl, —CO—N(($C_1$-$C_3$)-alkyl)$_2$, —COOH, —CO—O—($C_1$-$C_5$)-alkyl, heterocyclyl, and oxo;

$A_2$ represents a ringed structure consisting of aryl, heteroaryl, heterocyclyl or ($C_3$-$C_{10}$)-cycloalkyl;

$R_2$ is —$NR_5R_6$, or
aryl, heteroaryl, heterocyclyl, ($C_1$-$C_{10}$)-alkyl, ($C_3$-$C_{10}$)-cycloalkyl, ($C_1$-$C_{10}$)-alkenyl or ($C_1$-$C_{10}$)-alkynyl, each of which may be optionally substituted with one, two or three groups selected from halogen, —OH, aryl, heteroaryl, —O—($C_1$-$C_{10}$)-alkyl, —O—($C_1$-$C_7$)-alkyl-$R_7$, —O-aryl, —O-heteroaryl, —SH, —S—($C_1$-$C_{10}$)-alkyl, —S—($C_1$-$C_7$)-alkyl-$R_7$, —S-aryl, —S-heteroaryl, —P(O)(O—($C_1$–$C_5$)-alkyl)$_2$, —P(O)(OH)$_2$, —CN, —NR$_8$R$_9$, —CO—NH$_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

R$_3$ is one, two or three substituents independently selected from hydrogen, halogen, —CF$_3$, —OH, —O—($C_1$–$C_{10}$)-alkyl, —O—($C_1$–$C_7$)-alkyl-R$_7$, —O-aryl, —O-heteroaryl, —SH, —S—($C_1$–$C_{10}$)-alkyl, —S—($C_1$–$C_7$)-alkyl-R$_7$, —S-aryl, —S-heteroaryl, ($C_1$–$C_3$)-alkylene dioxy, —CN, —NO$_2$, —NR$_8$R$_9$, —CONR$_5$R$_6$, —COOH, —CO—O—($C_1$–$C_5$)-alkyl, heterocyclyl, —S(O)$_n$—($C_1$–$C_7$)-alkyl, —S(O)$_n$—aryl, —S(O)$_n$—heteroaryl, —S(O)$_n$—NR$_5$R$_6$ or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with up to five groups independently selected from halogen, —OH, aryl, heteroaryl, —O—($C_1$–$C_{10}$)-alkyl, —O—($C_1$–$C_7$)-alkyl-R$_7$, —O-aryl, —O-heteroaryl, —SH, —S—($C_1$–$C_{10}$)-alkyl, —S—($C_1$–$C_7$)-alkyl-R$_7$, —S-aryl, —S-heteroaryl, —P(O)(O—($C_1$–$C_5$)-alkyl)$_2$, —P(O)(OH)$_2$, —CN, —NR$_8$R$_9$, —CO—NH$_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

R$_5$ and R$_6$ independently are hydrogen, or ($C_1$–$C_{10}$)-alkyl, ($C_3$–$C_{10}$)-cycloalkyl, ($C_1$–$C_{10}$)-alkenyl or ($C_1$–$C_{10}$)-alkynyl, each of which is optionally substituted with one, two or three groups selected from aryl, heteroaryl, heterocyclyl, —CO—($C_1$–$C_{10}$)-alkyl, —CO-aryl, —CO-heteroaryl, —CO-heterocyclyl, —SO$_2$—($C_1$–$C_{10}$)-alkyl, —SO$_2$-aryl -SO$_2$-heteroaryl, or -SO$_2$-heterocyclyl; or R$_5$ and R$_6$ together with the nitrogen atom to which they are attached form a 5, 6, 7 or 8-membered carbocyclic ring up to two of which members are optionally hetero atoms selected from N, O, and S, the carbocyclic ring being optionally substituted with up to five groups selected from halogen, ($C_1$–$C_5$)-alkyl, ($C_3$–$C_6$)-cycloalkyl, ($C_1$–$C_5$)-alkenyl, ($C_1$–$C_5$)-alkynyl, ($C_1$–$C_3$)-hydroxyalkyl, ($C_1$–$C_3$)-alkyl-O—($C_1$–$C_4$)-alkyl, aryl, heteroaryl, —CF$_3$, —OH, —O—($C_1$–$C_7$)-alkyl, —O-aryl, —O-heteroaryl, —O—($C_2$–$C_4$)-alkyl-O—($C_1$–$C_7$)-alkyl, ($C_2$–$C_3$)-alkylenedioxy, —NR$_8$R$_9$, —CN, —CO—NH$_2$, —CO—NH—($C_1$–$C_3$)-alkyl, —CO—N(($C_1$–$C_3$)-alkyl)$_2$, —COOH, —CO—O—($C_1$–$C_5$)-alkyl, —CHO, CO—($C_1$–$C_5$)-alkyl, —S(O)$_n$—($C_1$–$C_4$)-alkyl, —S(O)$_n$—NH$_2$, —S(O)$_n$—NH—($C_1$–$C_3$)-alkyl, —S(O)$_n$—N(($C_1$–$C_3$)-alkyl)$_2$, oxo, —(CH$_2$)$_m$—NH$_2$, —(CH$_2$)$_m$—NH—($C_1$–$C_4$)-alkyl or —(CH$_2$)$_m$—N(($C_1$–$C_4$)-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or NR$_5$;

R$_7$ is —OH, —O—($C_1$–$C_7$)-alkyl, —NH$_2$, —NH—($C_1$–$C_4$)-alkyl, or

—N(($C_1$–$C_4$)-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or NR$_5$;

R$_8$ is hydrogen, or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with one, two or three groups selected from —OH, —O—($C_1$–$C_5$)-alkyl, —NH$_2$, —NH—($C_1$–$C_4$)-alkyl and —N(($C_1$–$C_4$)-alkyl)$_2$;

R$_9$ is hydrogen, —CO—($C_1$–$C_4$)-alkyl, or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with one, two or three groups selected from —OH, —O—($C_1$–$C_5$)-alkyl, —NH$_2$, —NH—($C_1$–$C_4$)-alkyl and —N(($C_1$–$C_4$)-alkyl)$_2$;

n is 0, 1, or 2; and m is 2, 3, or 4.

As used herein, "aryl" is an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), all of which may be substituted by one or several identical or different substituents from the group consisting of halogen, ($C_1$–$C_5$)-alkyl, phenyl, tolyl, —CF$_3$, —NO$_2$, —OH, —O—($C_1$–$C_5$)-alkyl, —O—($C_2$–$C_4$)-alkyl-O—($C_1$–$C_3$)-alkyl, ($C_1$–$C_2$)-alkylenedioxy, —NH$_2$, —NH—($C_1$–$C_3$)-alkyl, —N(($C_1$–$C_3$)-alkyl)$_2$, —NH—CHO, —NH—CO—($C_1$–$C_5$)-alkyl, —CN, —CO—NH$_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, —CHO, —CO—($C_1$–$C_5$)-alkyl, —S(O)$_n$—($C_1$–$C_4$)-alkyl, —S(O)$_n$-phenyl, —S(O)$_n$-tolyl, —S(O)$_2$—NH$_2$, —S(O)$_2$—NH—($C_1$–$C_3$)-alkyl and —S(O)$_2$—N(($C_1$–$C_3$)-alkyl)$_2$.

As used herein, "heteroaryl" is one or more aromatic ring systems of 5-, 6-, 7-, 8-, 9- or 10-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl.

A "carbocyclic group" "carbocycle" or "cycloalkyl" is a saturated or partially unsaturated cyclic ring or fused rings. Examples include cyclopropyl, cyclobutyl, and cycloheptyl. These rings may be substituted with one or more of the substituent groups mentioned above for aryl. The carbocyclic group may contain one or two heteroatoms selected from oxygen, sulfur, and nitrogen, and such ring systems may be referred to as "heterocyclyl" or "heterocyclic".

As used herein, "heterocyclyl" or "heterocyclic" includes monocyclic or polycyclic 5-membered to 11-membered saturated or partially unsaturated heterocycles that contain one or more ring heteroatoms selected from N, O, and S, and which may be substituted by one or more identical or different substituents selected from the group consisting of fluorine, ($C_1$–$C_5$)-alkyl, —OH, —O—(CI-C5)-alkyl, —O—($C_2$–$C_4$)-alkyl-O—($C_1$–$C_3$)-alkyl, —NH$_2$, —NH—($C_1$–$C_3$)-alkyl, —N(($C_1$–$C_3$)-alkyl)$_2$, —CN, —CO—NH$_2$, —CO—NH—($C_1$–$C_3$)-alkyl, —CO—N(($C_1$–$C_3$)-alkyl)$_2$, —COOH and —CO—O—($C_1$–$C_5$)-alkyl.

As used herein, "alkyl" includes straight-chain or branched hydrocarbon groups that may be optionally substituted with one or more of the substituents listed above for aryl, or from the group consisting of alkoxycarbonyl, alkoxy, or amino. Examples of alkyl groups include methyl, ethyl, propyl, butyl, pentyl, hexyl, heptyl, octyl, nonyl, decyl, the n-isomers of these groups, isopropyl, isobutyl, isopentyl, sec-butyl, tert-butyl, neopentyl, 3,3-dimethylbutyl.

"Alkenyl" means straight and branched hydrocarbon radicals having at least one double bond and includes ethenyl, propenyl, 1-but-3-enyl, 1-pent-3-enyl, 1-hex-5-enyl and the like. Examples of such groups include the vinyl group, 2-propylene (allyl), 2-butenyl, 2-methyl-2-propylene, ethinyl, 2-propinyl (propargyl), and 3-butinyl.

"Alkynyl" means straight and branched hydrocarbon radicals having one triple bond and includes ethynyl, propynyl, butynyl, pentyn-2-yl and the like.

By "alkoxy" in the present invention is meant straight or branched chain alkyl groups having 1–10 carbon atoms, attached through a divalent oxygen atom, and includes such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By "halogen" in the present invention is meant fluorine, bromine, chlorine, and iodine.

In another embodiment of the invention, compounds of the formula Ia are employed:

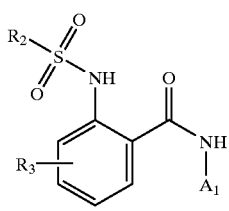

Ia wherein $R_2$, $R_3$, and $A_1$ are as defined above for formula I.

In yet another embodiment of the invention, compounds of the formula Ib are used:

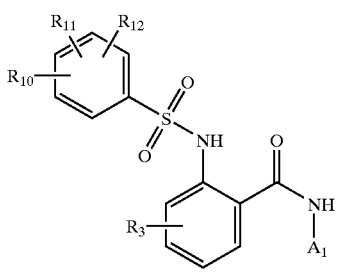

Ib wherein $A_1$ and $R_3$ are as defined above for formula I, and $R_{10}$, $R_{11}$ and $R_{12}$ independently represent from halogen, —OH, aryl, heteroaryl, —O—($C_1$-$C_{10}$)-alkyl, —O—($C_1$-$C_7$)-alkyl-$R_7$, —O-aryl, —O-heteroaryl, —SH, —S—($C_1$-$C_{10}$)-alkyl, —S—($C_1$-$C_7$)-alkyl-$R_7$, —S-aryl, —S-heteroaryl, —P(O)(O—($C_1$-$C_5$)-alkyl)$_2$, —P(O)(OH)$_2$, —CN, —$NR_8R_9$, —CO—$NH_2$, —CO—NH—($C_1$-$C_3$)-alkyl, —CO—N(($C_1$-$C_3$)-alkyl)$_2$, —COOH, —CO—O—($C_1$-$C_5$)-alkyl, heterocyclyl, or oxo. $R_7$, $R_8$ and $R_9$ are all as defined above for formula I.

In still another embodiment of the invention, compounds of the formula Ic are employed:

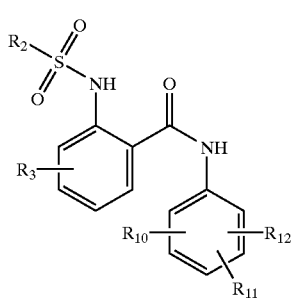

Ic wherein $R_2$ and $R_3$ are as defined above for formula I and $R_{10}$, $R_{11}$ and $R_{12}$ are as defined for formula Ib.

In another embodiment of the invention, compounds of the formula Id are employed:

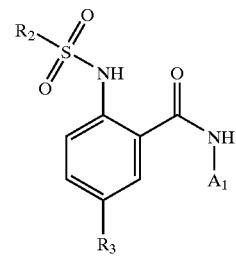

Id wherein $A_1$, $R_2$ and $R_3$ are as defined above for formula I.

In yet another embodiment of the invention, compounds of the formula Ie are employed:

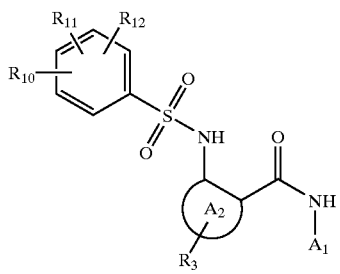

Ie wherein $A_1$, $A_2$ and $R_3$ are as defined above for formula I and $R_{10}$, $R_{11}$ and $R_{12}$ are as defined for formula Ib.

In still another embodiment of the invention, compounds of the formula If are used:

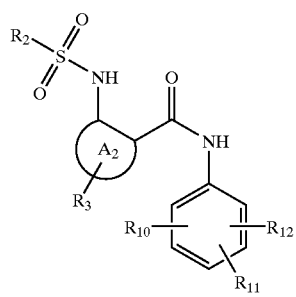

If wherein $A_2$, $R_2$ and $R_3$ are as defined above for formula I and $R_{10}$, $R_{11}$ and $R_{12}$ are as defined for formula Ib.

Preferred compounds according to this invention are compounds of the formula I, in which one or more of the groups contained therein have preferable meanings, wherein all combinations of preferable substituent definitions are the object of this invention. This invention also applies to all of the stereoisomer forms and mixtures, in all ratios, of all preferable compounds of the formula I, as well as their physiologically compatible salts.

Representative compounds of the invention are shown below in Table 1.

TABLE 1

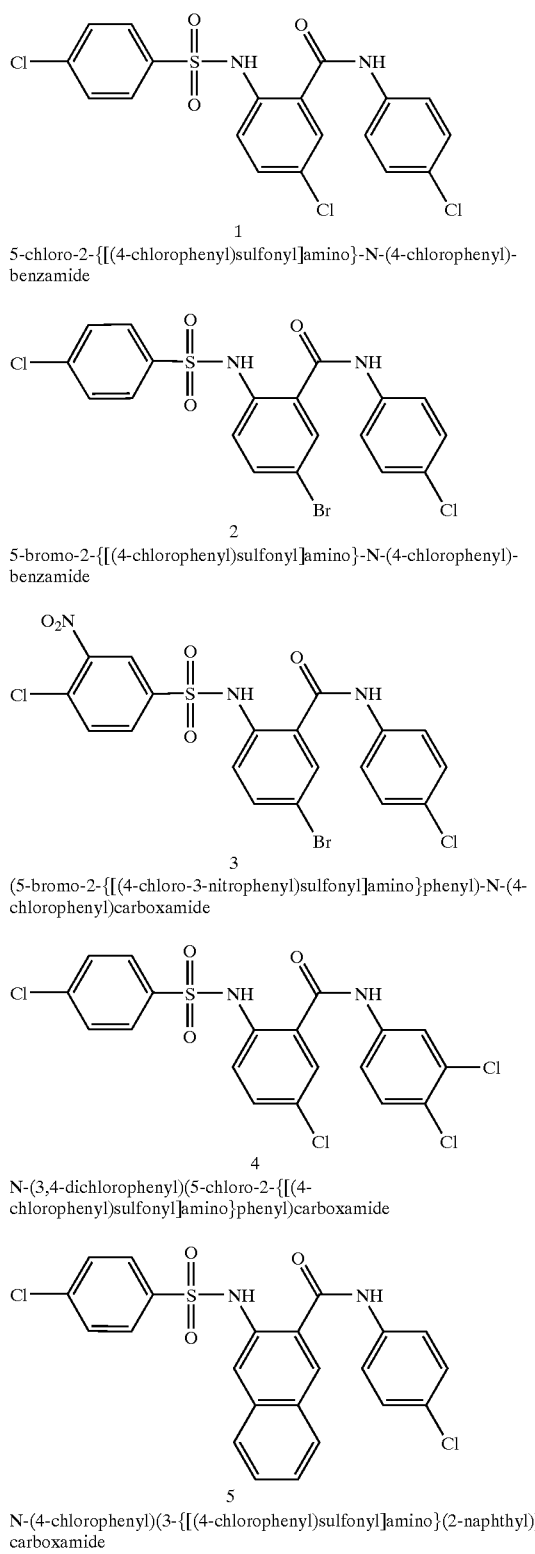

1
5-chloro-2-{[(4-chlorophenyl)sulfonyl]amino}-N-(4-chlorophenyl)-benzamide 2
5-bromo-2-{[(4-chlorophenyl)sulfonyl]amino}-N-(4-chlorophenyl)-benzamide 3
(5-bromo-2-{[(4-chloro-3-nitrophenyl)sulfonyl]amino}phenyl)-N-(4-chlorophenyl)carboxamide 4
N-(3,4-dichlorophenyl)(5-chloro-2-{[(4-chlorophenyl)sulfonyl]amino}phenyl)carboxamide 5
N-(4-chlorophenyl)(3-{[(4-chlorophenyl)sulfonyl]amino}(2-naphthyl))-carboxamide Representative compounds of the present invention, which are encompassed by Formula I, include, but are not limited to the compounds in Table I and their pharmaceutically acceptable salts.

The compounds disclosed herein can be prepared by any of the methods known in the art. Non-limiting examples of these methods include those disclosed in DE-A-35 23 705 and its equivalents. An example of a synthetic route for these compounds is described below (see Schindler, et. al., WO 00/02850).

According to Scheme 1 an aminocarboxylic acid of formula II can first be reacted with a sulfonyl chloride of the formula $R_2$—$SO_2$—Cl or a sulfonic acid anhydride, in a solvent such as water, pyridine, or an ether, in the presence of a base. The bases used may be common inorganic bases such as, for example, sodium carbonate or organic bases such as, for example, pyridine or triethylamine. The resulting sulfonylaminocarboxylic acid of formula III can then be converted to an acid chloride of formula IV, through reaction with a chlorinating agent as, for example, phosphorus pentachloride, phosphorus oxychloride, or thionyl chloride in an inert solution, and can then be reacted with an arylamine. The activation of the carboxylic acid group of the compounds of formula III can also follow a different reaction pathway, such as by means of one of the many methods known to a person skilled in the art that are used in peptide chemistry to establish amide bonds, such as through the use of a mixed anhydride, an activated ester, or by use of carbodiimides, such as dicyclohexylcarbodiimide.

The reaction of the activated sulfonylaminocarboxylic acid with an arylamine is completed preferably in an inert solution such as, for example, pyridine, tetrahydrofuran, or toluol with or without the addition of an inert auxiliary base, such as a tertiary amine or pyridine. If the arylamine used in the reaction with the activated carboxylic acid already contains the desired substituent or substituents $R_1$ in its $A_1$ group, (the arylamine is of the formula $A_1$-$NH_2$, wherein the $A_1$ group can contain, as specified above, one or more substituents $R_1$), the reaction scheme proceeds directly to the end product of formula I.

Scheme 1

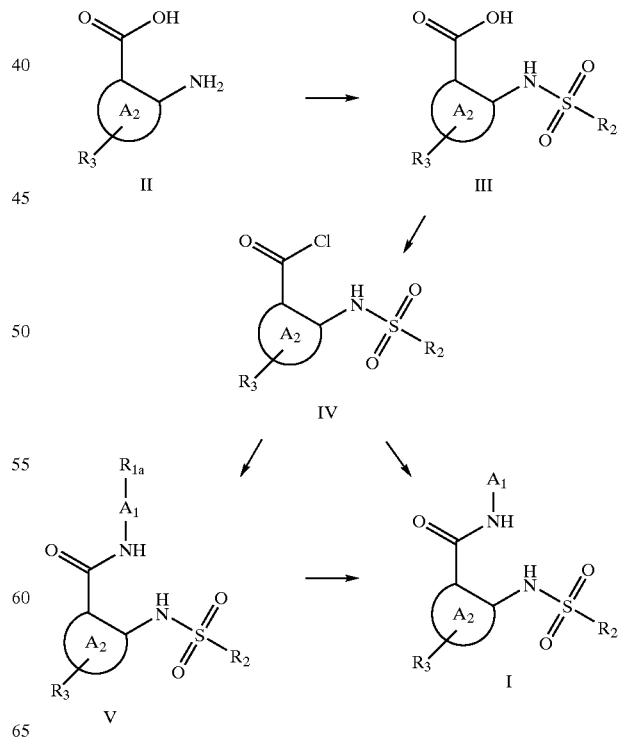

However, the activated carboxylic acid can also be converted initially with an arylamine of the formula $R_{1a}$-$A_1$-

$NH_2$, in which $R_{1a}$ represents hydrogen or one or more of the groups $R_1$, which can be contained in $A_1$ as substituents, or $R_{1a}$ represents one or more groups that can be converted into groups $R_1$ according to the above definition. For example, $R_{1a}$ can represent a hydrogen atom that is replaced in an electrophilic reaction with another group, such as a halogen atom or an aldehyde group. The conversion of the reaction product of formula V into a compound of formula I can take place according to standard procedures known in the art.

Compounds of formula I can also be obtained, for example, by initial activation of a substituted nitrocarboxylic acid of formula VI, such as by conversion into the corresponding acid chloride of formula VII or by other means, which is then, for example, reacted with a substituted arylamine of the formula $A_1$-$NH_2$, by methods analogous to those described above (see Scheme 2; Schindler, et al. WO 00/02850).

Before the nitro group is reduced to the amino group in the resulting nitro intermediate products of formula VIII, the activating effect of the nitro group on ring $A_2$ can be utilized, and a suitable group $R_3$, such as a halogen atom, can be replaced by another group $R_3$, such as an amine, by conversion with a nucleophile. The reduction of the nitro group to an amino group may take place, for example, by catalytic hydration in the presence of a precious metal catalyst or, preferably, in the presence of Raney nickel in a solvent such as ethanol, glacial acetic acid, or ethanolic hydrochloric acid, or by reduction with a non-precious metal such as tin, zinc, or iron in the presence of acid. The reduction can also be completed, for example, with tin(II)-chloride or by reduction with sodium dithionite, preferably, for example, in a mixture of methanol, tetrahydrofuran, and water as a solvent.

Scheme 2

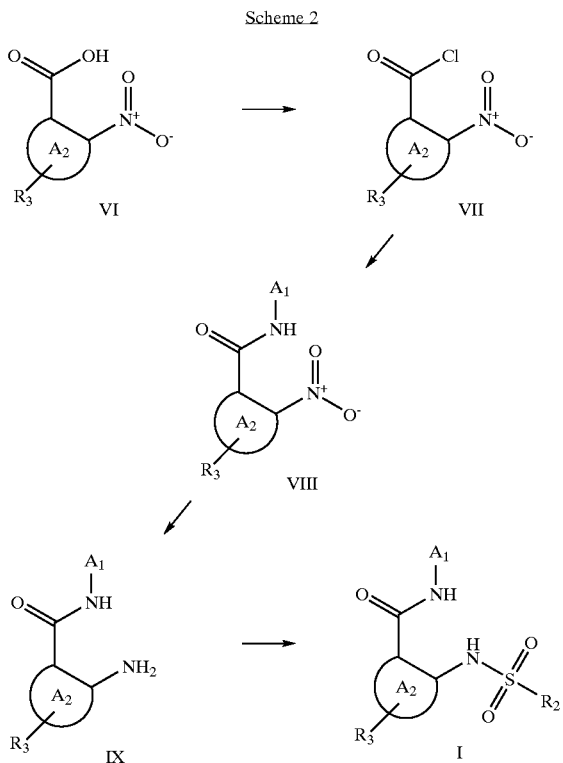

The sulfonylation of the amino group in the reduction product of formula IX with an activated sulfonic acid derivative by analogy to the reactions described above, such as with a sulfonic acid chloride in the presence of pyridine, ultimately produces the compound of formula I. Instead of an arylamine of the formula $A_1$-$NH_2$, an arylamine of the formula $R_{1a}$-$A_1$-$NH_2$ can be used, in which $R_{1a}$ has the meaning specified above, and the group or groups $R_{1a}$ can then be converted into the group or groups $R_1$.

A person of ordinary skill in the art is familiar with all the reactions for synthesis of compounds of formula I, which can be performed under standard conditions. Further details on this subject can be found, for example, in Houben-Weyl, Methods of Organic Chemistry, Thieme-Verlag, Stuttgart, or Organic Reactions, John Wiley & Sons, New York. Depending on the circumstances of each case, it may be advantageous or even necessary to block certain functional groups by introducing protective groups, and subsequently release these groups at a later step in the synthesis scheme, in order to avoid secondary reactions during the synthesis of compounds of formula I. One of skill in the art may also begin synthesis with functional groups in the form of precursor stages from which the desired functional group is generated in a later stage. These synthesis strategies are well known to a person of skill in the art. If necessary, the compounds of formula I can be isolated and purified using conventional methods, such as through the use of recrystallization or chromatography. The starting compounds used in the synthesis of the compounds of formula I are commercially available, or can be made according to the methods described in the literature, or by analogous methods.

The present compounds, or pharmaceutically acceptable salts, esters, amides, or prodrugs thereof, are useful in treating tumors from any tissue type. Examples of specific tumor types that the compounds may be used to treat include, but are not limited to, sarcomas, carcinomas, and mesotheliomas. The instant compounds can be administered individually or in combination, usually in the form of a pharmaceutical composition. Such compositions are prepared in a manner well known in the pharmaceutical art and comprise at least one active compound. Accordingly, a further aspect of the present invention also includes pharmaceutical compositions comprising as active ingredient compounds of the general formula I, associated with a pharmaceutically acceptable carrier. The invention further comprises the method of treating susceptible neoplasms using the compositions containing as an active ingredient one or more of the disclosed compounds.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.,* 1977;66:1–19 which is incorporated herein by reference.)

Examples of pharmaceutically acceptable, non-toxic esters of the compounds of this invention include $C_1$–$C_6$ alkyl esters, wherein the alkyl group is a straight or branched, substituted or unsubstituted, $C_5$–$C_7$ cycloalkyl esters, as well as arylalkyl esters such as benzyl and triphenylmethyl. $C_1$–$C_4$ alkyl esters are preferred, such as methyl, ethyl, 2,2,2-trichloroethyl, and tert-butyl. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines, wherein the alkyl groups are straight or branched. In the case of secondary amines, the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion of prodrugs is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

As used herein, the term "effective amount" means a dosage sufficient to produce a desired result. The desired result can be subjective or objective improvement in the recipient of the dosage, a decrease in tumor size, time to progression of disease, and/or survival.

The compounds of the invention can be administered as the sole active pharmaceutical agent, or they can be used in combination with one or more other anti-tumor agents. When administered as a combination, the therapeutic agents can be formulated as separate compositions that are given at the same time or different times, or the therapeutic agents can be given as a single composition.

The compounds may be made up in a solid form (including granules, powders or suppositories) or in a liquid form (e.g., solutions, suspensions, or emulsions). The compounds of the invention may be applied in a variety of solutions and may be subjected to conventional pharmaceutical operations such as sterilization and/or may contain conventional adjuvants, such as preservatives, stabilizers, wetting agents, emulsifiers, buffers etc.

For administration, the compounds are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinylpyrrolidine, and/or polyvinyl alcohol, and tableted or encapsulated for conventional administration. Alternatively, the compounds of this invention may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

Pharmaceutical compositions containing the compounds described herein are administered to an individual having a tumor. In therapeutic applications, compositions are administered to a human patient in an amount sufficient to cause regression of the tumor, or at least partially arrest tumorigenesis and metastasis. Amounts effective for this use depend on factors including, but not limited to, the nature of the compound (specific activity, etc.), the manner of administration, the stage and severity of the cancer, the weight and general state of health of the patient, and the judgment of the prescribing physician. The active compounds are effective over a wide dosage range. For example, dosages per day will normally fall within the range of about 1 µg/kg body weight to about 100 mg/kg of body weight. It will be understood that the amount of the compound actually administered will be determined by a physician, in the light of the relevant circumstances including the condition to be treated, the choice of compound to be administered, the chosen route of administration, the age, weight, and response of the individual patient, disorders affecting the heart, and other specific organ dysfunction, and therefore the above dosage ranges are not intended to limit the scope of the invention in any way.

The compounds of the invention may be administered by any suitable route, including orally, parentally, by inhalation or rectally in dosage unit formulations containing conventional pharmaceutically acceptable carriers, adjuvants, and vehicles, including liposomes. The term parenteral as used herein includes, subcutaneous, intravenous, intraarterial, intramuscular, intrasternal, intratendinous, intraspinal, intracranial, intrathoracic, infusion techniques, intracavity, or intraperitoneally.

In a preferred embodiment, the compounds of formula I are used for treating tumors from any tissue type. Examples of specific tumor types that the compounds may be used to treat include, but are not limited to, sarcomas, carcinomas, and mesotheliomas.

In yet further aspects, the invention provides an article of manufacture comprising packaging material and the above pharmaceutical compositions.

The instant invention may be embodied in other forms or carried out in other ways without departing from the spirit or essential characteristics thereof. The present disclosure and enumerated examples are therefore to be considered as in all respects illustrative and not restrictive, and all equivalency are intended to be embraced therein. One of ordinary skill in the art would be able to recognize equivalent embodiments of the instant invention, and be able to practice such embodiments using the teaching of the instant disclosure and only routine experimentation.

The disclosures in this application of all articles and references, including patents, are incorporated herein by reference.

The invention is illustrated further by the following examples which are not to be construed as limiting the invention in scope or spirit to the specific procedures described in them.

EXAMPLES

Example 1

Tissue Processing

Excess tissue specimens obtained from patients undergoing therapeutic surgical resections were freshly obtained at the time of surgery and a small portion of the specimen was sent for pathological testing. For diagnosis and grading of tissue samples (ie: prior to processing), hematoxylin and eosin stained tissue sections were examined by a pathologist. If the diagnosis and grading of the tissue concurred with the determination made by the surgical pathologist that provided the tissue, then the tissue was used in the screen. If there was no agreement, then two additional pathologists served as referees. If no consensus was reached, then the tissue was not used.

The remaining tissue was used to prepare cell suspensions. The tissue was initially treated enzymatically via standard methods until only undigested material remained. The digested cell suspension was filtered through one or more screens of between 40 micron and 100 micron porosity. The resulting cell suspension was further purified via isokinetic density centrifugation.

Additional normal cells were removed from the cell suspension by negative immunoselection with a combination of monoclonal antibodies linked to magnetic beads (Dynal) that were used according to the manufacturers' instructions. The remaining cells were placed into appropriate medium, frozen down in 1.0 mL aliquots, and stored until use.

Example 2

General Screen/Bioassay Procedures

After tissue processing, the relative purity of the resulting cell suspension was determined by cytological examination after fixation and Papanicolaou staining. Only those cell preparations greater than 80% tumor cells were used for testing of candidate compounds. If there was any doubt about the percentage of tumor cells in the cell preparation, additional pathologists served as referees to make a determination.

Cell preparations that passed histological and cytological examination for diagnosis, grading, and cell purity were thawed at 37° C. and resuspended in tissue culture medium designed to maintain the cells during the incubation period. The live and dead cells were counted and the cells were diluted in culture medium to $1.0 \times 10^3$ live cells/test well for tumor cells and $3.3 \times 10^3$ live cells/test well for normal cells.

The cells were added to microtiter plates and incubated at 37° C. overnight with 10 μM of the candidate compounds that were added at 1/10th the volume of the cell suspension. Alamar Blue (Accumed International, Westlake Ohio) was then added to the cells at 1/10 the volume of the well, and the cells were further incubated at 37° C. for various times. Alamar Blue dye measures cellular re-dox reactions (ie: cellular respiration) whereby a spectral shift occurs upon reduction of the dye. (Excitation 530 nm; emission 590 nm).

The kinetics of cellular re-dox reactions were subsequently measured at various times, for example at 3 hours, 3 days, and 5 days post-dye addition. These measurements, in comparison with control cells (untreated with compound) and media controls (test wells without cells) provide the percent inhibition of cellular mitochondrial respiration as a result of candidate compound treatment, as well as $IC_{50}$ determinations.

The Alamar Blue data were subsequently confirmed by microscopic observation, and by the use of calcein AM (Molecular Probes, Eugene Oreg.), a cell permeant esterase substrate that measures both esterase activity and cell membrane activity. If the cell is alive, the dye is converted into a fluorogenic substrate by intracellular esterases and is retained by the cell (excitation 485 nm; emission 530 nm). If the cells are dead, the calcein AM rapidly leaks from the cells and is not converted into a fluorogenic substrate. Thus, the assay is useful for cytotoxicity testing.

Example 3

Anti-Tumor Screen

In a blinded fashion, approximately 10,000 compounds were tested at a rate of 1,000–4,000 compounds per run set against various tumor types. The anti-tumor screen utilized was composed of three tiers as follows. In screen 1, patient tumor cells were tested in singles, with candidate compounds at a concentration of 10 μM. Samples that showed at least 80% inhibition (compared to cell and media controls) and/or two standard deviations from the mean of the plate samples were advanced. In the first part of the second test (screen 2a), the compounds were re-tested, in duplicate, at 10 μM concentrations on patient tumors. Compounds that re-confirmed were then tested, in duplicate, at 10 μM concentration on patient normal cells. Samples that exhibited at least 80% inhibition on tumor cells and no more than 20% inhibition of normal cells were tested in the second part (screen 2b).

Compound 1, (5-chloro-2-{[(4-chlorophenyl)sulfonyl]amino}-N-(4-chlorophenyl)benzamide), was shown to have selectivity against tumor cells in the above screen, and was further tested against other tumor types. The anti-tumor screen utilized was composed of three tiers as discussed above. In screen 1, patient tumor cells were tested, with compound 1 at a concentration of 10 μM. Compound 1 showed at least 80% inhibition (compared to cell and media controls) and/or two standard deviations from the mean of the plate samples, and was advanced. In the second test (screen 2), compound 1 was re-tested, in duplicate, at 10 μM concentrations on patient tumors. Compound 1 re-confirmed and was then tested, in duplicate, at 10 μM concentration on patient normal cells, on which it exhibited at least 80% inhibition on tumor cells and no more than 20% inhibition of normal cells. Compound 1 was then tested for $IC_{50}$, in triplicate, on both patient tumor and patient normal cells for the concentration at which tumor cell processes were inhibited 50% vs. untreated tumor cells.

A summary of the results from this screen is shown below in Table 2:

TABLE 2

| Tumor # | Tumor Type/Location | IC50 (nM) |
| --- | --- | --- |
| 1 | Leiomyosarcoma/abdominal | 170 |
| 1 | Leiomyosarcoma/abdominal | 150 |
| 2 | Fibrohistiocytic Sarcoma/lung | 30 |
| 3 | Myxofibrosarcoma/thigh | 49 |
| 3 | Myxofibrosarcoma/thigh | 49 |
| 4 | Leiomyosarcoma/pelvic | 339 |
| 4 | Leiomyosarcoma/pelvic | 339 |
| 4 | Leiomyosarcoma/pelvic | 410 |
| 5 | Gastrointestinal stromal tumor (sarcoma) | 2400 |
| 6 | Gastrointestinal stromal tumor (sarcoma) | 531 |
| 7 | Ovarian | 35 |

Taken together, the data shows that compound 1 exhibits good anti-tumor activity potency against a variety of tumor types.

Example 4

Identification of Additional Anti-Tumor Compounds

In an effort to identify further compounds structurally related to compound 1 that exhibited similar or improved anti-tumor efficacy, a series of structurally related sulfonylamino-substituted N-aryl- or heteroarylcarboxamide derivatives were tested as in Example 3, on tumor #4 in Table 2. Results are depicted below in Table 3.

TABLE 3

| COMPOUND | IC50 (nM) | TUMOR TYPE |
|---|---|---|
| 2 | 44.7 | Leiomyosarcoma/pelvic |
| 3 | 118 | Leiomyosarcoma/pelvic |
| 4 | 12.4; 74.3 | Leiomyosarcoma/pelvic |
| 5 | 209 | Leiomyosarcoma/pelvic |

Based on the above data, the present invention unexpectedly provides needed methods, compounds, and pharmaceutical compositions for treating tumors.

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A method for treating a tumor in a subject in need thereof, wherein the tumor is selected from the group consisting of sarcomas, carcinomas, and mesotheliomas, comprising administering to said subject a therapeutically effective amount of a compound having the formula:

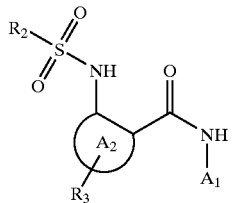

or a pharmaceutically acceptable salt, ester, or amide thereof wherein $A_1$ is phenyl which may be optionally substituted with one, two or three groups independently selected from halogen, aryl, —$CF_3$, —$NO_2$, —OH, —O—($C_1$-$C_7$)-alkyl, —O—($C_2$-$C_4$)-alkyl-O—($C_1$-$C_7$)-alkyl, —O-aryl, ($C_1$-$C_2$)-alkylenedioxy, —$NR_5R_6$, —CN, —CO—$NR_5R_6$, —COOH, —CO—O—($C_1$-$C_5$)-alkyl, heterocyclyl, —CHO, —CO—($C_1$-$C_{10}$)-alkyl, —CO-aryl, —CO-heteroaryl, or
($C_1$-$C_{10}$)-alkyl, ($C_3$-$C_{120}$)-cycloalkyl, ($C_1$-$C_{10}$)-alkenyl or ($C_1$-$C_{10}$)-alkynyl, each of which is optionally substituted with up to five groups independently selected front halogen, —OH, aryl, heteroaryl, —O—($C_1$-$C_{10}$)-alkyl, —O—($C_1$-$C_7$)-alkyl-$R_7$, —O-aryl, —O-heteroaryl, —SH, —S—($C_1$-$C_{10}$)-alkyl, —S—($C_1$-$C_7$)-alkyl-$R_7$, —S-aryl, —S-heteroaryl, —P(O)(O—($C_1$-$C_5$)-alkyl)$_2$, —P(O)(OH)$_2$, —CN, —$NR_8R_9$, —CO—$NH_2$, —CO—NH—($C_1$-$C_3$)-alkyl, —CO—N(($C_1$-$C_3$)-alkyl)$_2$, —COOH, —CO—O—($C_1$-$C_5$)-alkyl, heterocyclyl, and oxo;

$A_2$ is phenyl;

$R_2$ is phenyl which may be optionally substituted with one, two or three groups selected from halogen, —OH, aryl, heteroaryl, —O—($C_1$-$C_{10}$)-alkyl, —O—($C_1$-$C_7$)-alkyl-$R_7$, —O-aryl, —O-heteroaryl, —SH, —S—($C_1$-$C_{10}$)-alkyl, —S—($C_1$-$C_7$)-alkyl-$R_7$, —S-aryl, —S-heteroaryl, —P(O)(O—)($C_1$-$C_5$)-alkyl)$_2$, —P(O)(OH)$_2$, —CN, —$NR_8R_9$, —CO—$NH_2$, —CO—NH—($C_1$-$C_3$)-alkyl, —CO—N(($C_1$-$C_3$)-alkyl)$_2$, —COOH, —CO—O—($C_1$-$C_5$)-alkyl, heterocyclyl, and oxo;

$R_3$ is one, two or three substituents independently selected from hydrogen, halogen, —$CF_3$, —OH, —O—($C_1$-$C_{10}$)-alkyl, —O—($C_1$-$C_7$)-alkyl-$R_7$, —O-aryl, —O-heteroaryl, —SH, —S—($C_1$-$C_{10}$)-alkyl, —S—($C_1$-$C_7$)-alkyl-$R_7$, —S-aryl, —S-heteroaryl, ($C_1$-$C_3$)-alkylene dioxy, —CN, —$NO_2$, —$NR_8R_9$, —$CONR_5R_6$, —COOH, —CO—O—($C_1$-$C_5$)-alkyl, heterocyclyl, —S(O)$_n$—($C_1$-$C_7$)-alkyl, —S(O)$_n$-aryl, —S(O)$_n$-heteroaryl, —S(O)$_n$—$NR_5R_6$, or
($C_1$-$C_7$)-alkyl, ($C_3$-$C_7$)-cycloalkyl, ($C_1$-$C_7$)-alkenyl or ($C_1$-$C_7$)-alkynyl, each of which is optionally substituted with up to five groups independently selected from halogen, —OH, aryl, heteroaryl, —O—($C_1$-$C_{10}$)-alkyl, —O—($C_1$-$C_7$)-alkyl-$R_7$, —S-aryl, —S-heteroaryl, —P(O)(O—($C_1$-$C_5$)-alkyl)$_2$, —P(O)(OH)$_2$, —CN, —$NR_8R_9$, —CO—$NH_2$, —CO—NH—($C_1$-$C_3$)-alkyl, —CO—N(($C_1$-$C_3$)-alkyl)$_2$, —COOH, —CO—O—($C_1$-$C_5$)-alkyl, heterocyclyl, and oxo;

$R_5$ and $R_0$ independently are hydrogen, or
($C_1$-$C_{10}$)-alkyl, ($C_3$-$C_{10}$)-cycloalkyl, ($C_1$-$C_{10}$)-alkenyl or ($C_1$-$C_{10}$)-alkynyl, each of which is optionally substituted with one, two or three groups selected from aryl, heteroaryl, heterocyclyl, —CO—($C_1$-$C_{10}$)-alkyl, —CO-aryl, —CO-heteroaryl, —CO-heterocyclyl, —$SO_2$—($C_1$-$C_{10}$)-alkyl, —$SO_2$-aryl —$SO_2$-heteroaryl, or —$SO_2$-heterocyclyl; or $R_5$ and $R_6$ together with the nitrogen atom to which they are attached form a 5, 6, 7 or 8-membered carbocyclic ring up to two of which members are optionally hetero atoms selected front N, O, and S, the carbocyclic ring being optionally substituted with up to five groups selected from halogen, ($C_1$-$C_5$)-alkyl, ($C_3$-$C_6$)-cycloalkyl, ($C_1$-$C_5$)-alkenyl, ($C_1$-$C_5$)-alkynyl, ($C_1$-$C_3$)-hydroxyalkyl, ($C_1$-$C_3$)-alkyl-O—($C_1$-$C_4$)-alkyl, aryl, heteroaryl, —$CF_3$, —OH, —O—($C_1$-$C_7$-alkyl, —O-aryl, —O-heteroaryl, —O—($C_2$-$C_4$-alkyl-O—($C_1$-$C_7$)-alkyl, ($C_2$-$C_3$)-alkylenedioxy, —$NR_8R_9$, —CN, —CO—$NH_2$, —CO—NH—($C_1$-$C_3$)-alkyl, —CO—N(($C_1$-$C_3$)-alkyl)$_2$, —COOH, —CO—O—($C_1$-$C_5$)-alkyl, —CHO, CO—($C_1$-$C_5$)alkyl, —S(O)$_n$—($C_1$-$C_4$)-alkyl, S(O)$_n$—$NH_2$, —S(O)$_n$—NH—($C_1$-$C_3$)-alkyl, —S(O)$_n$—N(($C_1$-$C_3$)-alkyl)$_2$, oxo, —($CH_2$)$_m$—$NH_2$, —($CH_2$)$_m$—NH—($C_1$-$C_4$)-alkyl or
—($CH_2$)$_m$—N(($C_1$-$C_4$)-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_7$ is —OH, —O—$(C_1-C_7)$-alkyl, —$NH_2$, —NH—$(C_1-C_4)$-alkyl, or
—N$((C_1-C_4$-alkyl$))_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_8$ is hydrogen, or
$(C_1-C_7)$-alkyl, $(C_3-C_7)$-cycloalkyl, $(C_1-C_7)$-alkenyl or $(C_1-C_7)$-alkynyl, each of which is optionally substituted with one, two or three groups selected from —OH, —O—$(C_1-C_5)$-alkyl, —$NH_2$, —NH—$(C_1-C_4$-alkyl and —N$((C_1-C_4$-alkyl$))_2$;

$R_9$ is hydrogen, —CO—$(C_1-C_4)$-alkyl, or
$(C_1-C_7)$-alkyl, $(C_3-C_7)$-cycloalkyl, $(C_1-C_7)$-alkenyl or $(C_1-C_7)$-alkynyl, each of which is optionally substituted with one, two or three groups selected from —OH, —O—$(C_1-C_5)$-alkyl, —$NH_2$, —NH—$(C_1-C_4)$-alkyl and —N$((C_1-C_4$-alkyl$))_2$;

n is 0, 1, or 2; and
m is 2, 3, or 4.

2. A method for treating a tumor in a subject in need thereof, wherein the tumor is selected from the group consisting of sarcomas, carcinomas, and mesotheliomas, comprising administering to said subject a therapeutically effective amount of a compound having the formula:

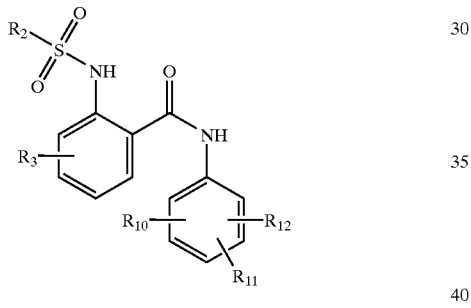

or a pharmaceutically acceptable salt, ester, or amide thereof wherein
$R_2$ is phenyl which may be optionally substituted with one, two or three groups selected from halogen, —OH, aryl, heteroaryl, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, —P(O)(O—$(C_1-C_5)$-alkyl$)_2$, —P(O)(OH$)_2$, —CN, —$NR_8R_9$, —CO—$NH_2$, —CO—NH—$(C_1-C_3$-alkyl, —CO—N$((C_1-C_3)$-alkyl$)_2$, —COOH, —CO—O—$(C_1-C_5)$-alkyl, heterocyclyl, and oxo, $R_3$ is one, two or three substituents independently selected from hydrogen, halogen, —$CF_3$, —OH, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, $(C_1-C_3)$-alkylene dioxy, —CN, —$NO_2$, —$NR_8R_9$, —$CONR_5R_6$, —COOH, —CO—O—$(C_1-C_5)$-alkyl, heterocyclyl, —S(O)$_n$—$(C_1-C_7)$-alkyl, —S(O)$_n$-aryl, —S(O)$_n$-heteroaryl, —S(O)$_n$—$NR_5R_6$, or
$(C_1-C_7)$-alkyl, $(C_3-C_7)$-cycloalkyl, $(C_1-C_7)$-alkenyl or $(C_1-C_7)$-alkynyl, each of which is optionally substituted with up to five groups independently selected from halogen, —OH, aryl, heteroaryl, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, —P(O)(O—$(C_1-C_5)$-alkyl$)_2$, —P(O)(OH$)_2$, —CN, —$NR_8R_9$, —CO—$NH_2$, —CO—NH—$(C_1-C_3)$-alkyl, —CO—N$((C_1-C_3)$-alkyl$)_2$, —COOH, —CO—O—$(C_1-C_5)$-alkyl, heterocyclyl, and oxo;

$R_5$ and $R_6$ independently are hydrogen, or
$(C_1-C_{10})$-alkyl, $(C_3-C_{10})$-cycloalkyl, $(C_1-C_{10})$-alkenyl or $(C_1-C_{10})$-alkynyl, each of which is optionally substituted with one, two or three groups selected from aryl, heteroaryl, heterocyclyl, —CO—$(C_1-C_{10})$-alkyl, —CO-aryl, —CO-heteroaryl, —CO-heterocyclyl, —$SO_2$—$(C_1-C_{10})$-alkyl, —$SO_2$—aryl —$SO_2$-heteroaryl, or —$SO_2$-heterocyclyl; or $R_5$ and $R_6$ together with the nitrogen atom to which they are attached form a 5, 6, 7 or 8-membered carbocyclic ring up to two of which members are optionally hetero atoms selected from N, O, and S, the carbocyclic ring being optionally substituted with up to five groups selected from halogen, $(C_1-C_5)$-alkyl, $(C_3-C_6)$-cycloalkyl, $(C_1-C_5)$-alkenyl, $(C_1-C_5)$-alkynyl, $(C_1-C_3)$-hydroxyalkyl, $(C_1-C_3)$-alkyl-O—$(C_1-C_4)$-alkyl, aryl, heteroaryl, —$CF_3$, —OH, —O—$(C_1-C_7)$-alkyl, —O-aryl, —O-heteroaryl, —O—$(C_2-C_4)$-alkyl-O—$(C_1-C_7)$-alkyl, $(C_2-C_3)$-alkylenedioxy, —$NR_8R_9$, —CN, —CO—$NH_2$, —CO—NH—$(C_1-C_3)$-alkyl, —CO—N$((C_1-C_3)$-alkyl$)_2$, —COOH, —CO—O—$(C_1-C_5)$-alkyl, —CHO, CO—$(C_1-C_5)$-alkyl, —S(O)$_n$—$(C_1-C_4)$-alkyl, S(O)$_n$—$NH_2$, —S(O)$_n$—NH—$(C_1-C_3)$-alkyl, —S(O)$_n$—N$((C_1-C_3)$-alkyl$)_2$, oxo, —$(CH_2)_m$—$NH_2$, —$(CH_2)_m$—NH—$(C_1-C_4)$-alkyl or
—$(CH_2)_m$—N$((C_1-C_4$-alkyl$))_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_7$ is —OH, —O—$(C_1-C_7)$-alkyl, —$NH_2$, —NH—$(C_1-C_4)$-alkyl, or
—N$((C_1-C_4$-alkyl$))_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_8$ is hydrogen, or
$(C_1-C_7)$-alkyl, $(C_3-C_7)$-cycloalkyl, $(C_1-C_7)$-alkenyl or $(C_1-C_7)$-alkynyl, each of which is optionally substituted with one, two or three groups selected from —OH, —O—$(C_1-C_5)$-alkyl, —$NH_2$, —NH—$(C_1-C_4$-alkyl and —N$((C_1-C_4$-alkyl$))_2$;

$R_9$ is hydrogen, —CO—$(C_1-C_4)$-alkyl, or
$(C_1-C_7)$-alkyl, $(C_3-C_7)$-cycloalkyl, $(C_1-C_7)$-alkenyl or $(C_1-C_7)$-alkynyl, each of which is optionally substituted with one, two or three groups selected from —OH, —O—$(C_1-C_5)$-alkyl, —$NH_2$, —NH—$(C_1-C_4)$-alkyl and —N$((C_1-C_4$-alkyl$))_2$;

$R_{10}$, $R_{11}$ and $R_{12}$ independently represent halogen, —OH, aryl, heteroaryl, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, —P(O)$(C_1-C_5)$-alkyl$)_2$, —P(O)(OH$)_2$, —CN, —CO—O—$(C_1-C_5)$-alkyl heterocyclyl, or oxo;

n is 0, 1, or 2; and
m is 2, 3, or 4.

3. A method for treating a tumor in a subject in need thereof, wherein the tumor is selected from the group consisting of sarcomas, carcinomas, and mesotheliomas, comprising administering to said subject a therapeutically effective amount of a compound having the formula:

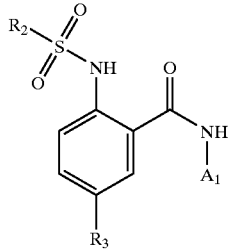

or a pharmaceutically acceptable salt, ester, or amide thereof wherein $A_1$ is phenyl which may be optionally substituted with one, two or three groups independently selected from halogen, aryl, —$CF_3$, —$NO_2$, —OH, —O—($C_1$–$C_7$)-alkyl, —O—($C_2$–$C_4$)-alkyl-O—($C_1$–$C_7$)-alkyl, —O-aryl, ($C_1$–$C_2$)-alkylenedioxy, —$NR_5R_6$, —CN, —CO—$NR_5R_6$, —COOH, —CO—O—($C_1$–$C_5$)-alkyl, heterocyclyl, —CHO, —CO—($C_1$–$C_{10}$)-alkyl, —CO-aryl, —CO-heteroaryl, or ($C_1$–$C_{10}$)-alkyl, ($C_3$–$C_{120}$)-cycloalkyl, ($C_1$–$C_{10}$)-alkenyl or ($C_1$–$C_{10}$)-alkynyl, each of which is optionally substituted with up to five groups independently selected front halogen, —OH, aryl, heteroaryl, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, —P(O)(O—($C_1$–$C_5$)-alkyl)$_2$, —P(O)(OH)$_2$, —CN, —$NR_8R_9$, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

$R_2$ is phenyl which may be optionally substituted with one, two or three groups selected from halogen, —OH, aryl, heteroaryl, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, —P(O)(O—)($C_1$–$C_5$)-alkyl)$_2$, —P(O)(OH)$_2$, —CN, —$NR_8R_9$, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

$R_3$ is one, two or three substituents independently selected from hydrogen, halogen, —$CF_3$, —OH, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, ($C_1$–$C_3$)-alkylene dioxy, —CN, —$NO_2$, —$NR_8R_9$, —$CONR_5R_6$, —COOH, —CO—O—($C_1$–$C_5$)-alkyl, heterocyclyl, —S(O)$_n$—($C_1$–$C_7$)-alkyl, —S(O)$_n$-aryl, —S(O)$_n$-heteroaryl, —S(O)$_n$—$NR_5R_6$, or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with up to five groups independently selected from halogen, —OH, aryl, heteroaryl, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, —P(O)(O—($C_1$–$C_5$)-alkyl)$_2$, —P(O)(OH)$_2$, —CN, —$NR_8R_9$, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

$R_5$ and $R_6$ independently are hydrogen, or ($C_1$–$C_{10}$)-alkyl, ($C_3$–$C_{10}$)-cycloalkyl, ($C_1$–$C_{10}$)-alkenyl or ($C_1$–$C_{10}$)-alkynyl, each of which is optionally substituted with one, two or three groups selected from aryl, heteroaryl, heterocyclyl, —CO—($C_1$–$C_{10}$)-alkyl, —CO-aryl, —CO-heteroaryl, —CO-heterocyclyl, —$SO_2$—($C_1$–$C_{10}$)-alkyl, —$SO_2$-aryl —$SO_2$-heteroaryl, or —$SO_2$-heterocyclyl; or $R_5$ and $R_6$ together with the nitrogen atom to which they are attached form a 5, 6, 7 or 8-membered carbocyclic ring up to two of which members are optionally hetero atoms selected front N, O, and S, the carbocyclic ring being optionally substituted with up to five groups selected from halogen, ($C_1$–$C_5$)-alkyl, ($C_3$–$C_6$)-cycloalkyl, ($C_1$–$C_5$)-alkenyl, ($C_1$–$C_5$)-alkynyl, ($C_1$–$C_3$)-hydroxyalkyl, ($C_1$–$C_3$)-alkyl-O—($C_1$–$C_4$)-alkyl, aryl, heteroaryl, —$CF_3$, —OH, —O—($C_1$–$C_7$-alkyl, —O-aryl, —O-heteroaryl, —O—($C_2$–$C_4$)-alkyl-O—($C_1$–$C_7$)-alkyl, ($C_2$–$C_3$)-alkylenedioxy, —$NR_8R_9$, —CN, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, —CHO, CO—($C_1$–$C_5$)-alkyl, —S(O)$_n$—($C_1$–$C_4$)-alkyl, —S(O)$_n$—$NH_2$, —S(O)$_n$—NH—($C_1$–$C_3$)-alkyl, —S(O)$_n$—N(($C_1$–$C_3$)-alkyl)$_2$, oxo, —($CH_2$)$_m$—$NH_2$, —($CH_2$)$_m$—NH—($C_1$–$C_4$)-alkyl or —($CH_2$)$_m$—N(($C_1$–$C_4$)-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_7$ is —OH, —O—($C_1$–$C_7$)-alkyl, —$NH_2$, —NH—($C_1$–$C_4$)-alkyl, or

—N(($C_1$–$C_4$-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_8$ is hydrogen, or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with one, two or three groups selected from —OH, —O—($C_1$–$C_5$)-alkyl, —$NH_2$, —NH—($C_1$–$C_4$-alkyl and —N(($C_1$–$C_4$-alkyl)$_2$;

$R_9$ is hydrogen, —CO—($C_1$–$C_4$)-alkyl, or ($C_1$–$C_7$)-alkyl, ($C_3$–$C_7$)-cycloalkyl, ($C_1$–$C_7$)-alkenyl or ($C_1$–$C_7$-alkynyl, each of which is optionally substituted with one, two or three groups selected from —OH, —O—($C_1$–$C_5$)-alkyl, —$NH_2$, —NH—($C_1$–$C_4$-alkyl and —N(($C_1$–$C_4$-alkyl)$_2$;

n is 0, 1, or 2; and m is 2, 3, or 4.

4. A method for treating a tumor in a subject in need thereof, wherein the tumor is selected from the group consisting of sarcomas, carcinomas, and mesotheliomas, comprising administering to said subject a therapeutically effective amount of a compound having the formula:

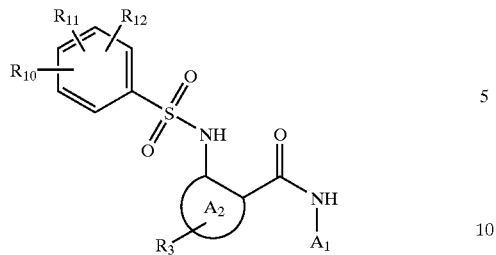

or a pharmaceutically acceptable salt, ester, or amide thereof wherein $A_1$ is phenyl which may be optionally substituted with one, two or three groups independently selected from halogen, aryl, —$CF_3$, —$NO_2$, —OH, —O—($C_1$–$C_7$)-alkyl, —O—($C_2$–$C_4$)-alkyl-O—($C_1$–$C_7$)-alkyl, —O-aryl, ($C_1$–$C_2$)-alkylenedioxy, —$NR_5R_6$, —CN, —CO—$NR_5R_6$, —COOH, —CO—O—($C_1$–$C_5$)-alkyl, heterocyclyl, —CHO, —CO—($C_1$–$C_{10}$)-alkyl, —CO-aryl, —CO-heteroaryl, or ($C_1$–$C_{10}$)-alkyl, ($C_3$–$C_{10}$)-cycloalkyl, ($C_1$–$C_{10}$)-alkenyl or ($C_1$–$C_{10}$)-alkynyl, each of which is optionally substituted with up to five groups independently selected front halogen, —OH, aryl, heteroaryl, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, —P(O)(O—($C_1$–$C_5$)-alkyl)$_2$, —P(O)(OH)$_2$, —CN, —$NR_8R_9$, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

$A_2$ is phenyl;

$R_3$ is one, two or three substituents independently selected from hydrogen, halogen, —$CF_3$, —OH, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, ($C_1$–$C_3$)-alkylene dioxy, —CN, —$NO_2$, —$NR_8R_9$, —$CONR_5R_6$, —COOH, —CO—O—($C_1$–$C_5$)-alkyl, heterocyclyl, —S(O)$_n$—($C_1$–$C_7$)-alkyl, —S(O)$_n$-aryl, —S(O)$_n$-heteroaryl, —S(O)$_n$—$NR_5R_6$, or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with up to five groups independently selected from halogen, —OH, aryl, heteroaryl, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, —P(O)(O—($C_1$–$C_5$)-alkyl)$_2$, —P(O)(OH)$_2$, —CN, —$NR_8R_9$, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, heterocyclyl, and oxo;

$R_5$ and $R_6$ independently are hydrogen, or ($C_1$–$C_{10}$)-alkyl, ($C_3$–$C_{10}$)-cycloalkyl, ($C_1$–$C_{10}$)-alkenyl or ($C_1$–$C_{10}$)-alkynyl, each of which is optionally substituted with one, two or three groups selected from aryl, heteroaryl, heterocyclyl, —CO—($C_1$–$C_{10}$)-alkyl, —CO-aryl, —CO-heteroaryl, —CO-heterocyclyl, —$SO_2$—($C_1$–$C_{10}$)-alkyl, —$SO_2$-aryl —$SO_2$-heteroaryl, or —$SO_2$-heterocyclyl; or $R_5$ and $R_6$ together with the nitrogen atom to which they are attached form a 5, 6, 7 or 8-membered carbocyclic ring up to two of which members are optionally hetero atoms selected front N, O, and S, the carbocyclic ring being optionally substituted with up to five groups selected from halogen, ($C_1$–$C_5$)-alkyl, ($C_3$–$C_6$)-cycloalkyl, ($C_1$–$C_5$)-alkenyl, ($C_1$–$C_5$)-alkynyl, ($C_1$–$C_3$)-hydroxyalkyl, ($C_1$–$C_3$)-alkyl-O—($C_1$–$C_4$)-alkyl, aryl, heteroaryl, —$CF_3$, —OH, —O—($C_1$–$C_7$-alkyl, —O-aryl, —O-heteroaryl, —O—($C_2$–$C_4$-alkyl-O—($C_1$–$C_7$)-alkyl, ($C_2$–$C_3$)-alkylenedioxy, —$NR_8R_9$, —CN, —CO—$NH_2$, —CO—NH—($C_1$–$C_3$)-alkyl, —CO—N(($C_1$–$C_3$)-alkyl)$_2$, —COOH, —CO—O—($C_1$–$C_5$)-alkyl, —CHO, CO—($C_1$–$C_5$)alkyl, —S(O)$_n$—($C_1$–$C_4$)-alkyl, —S(O)$_n$—$NH_2$, —S(O)$_n$—NH—($C_1$–$C_3$)-alkyl, —S(O)$_n$—N(($C_1$–$C_3$)-alkyl)$_2$, oxo, —($CH_2$)$_m$—$NH_2$, —($CH_2$)$_m$—NH—($C_1$–$C_4$)-alkyl or —($CH_2$)$_m$—N(($C_1$–$C_4$)-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_7$ is —OH, —O—($C_1$–$C_7$)-alkyl, —$NH_2$, —NH—($C_1$–$C_4$)-alkyl, or

—N(($C_1$–$C_4$-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_8$ is hydrogen, or ($C_1$–$C_7$)-alkyl, ($C_3$–$C_7$)-cycloalkyl, ($C_1$–$C_7$)-alkenyl or ($C_1$–$C_7$)-alkynyl, each of which is optionally substituted with one, two or three groups selected from —OH, —O—($C_1$–$C_5$)-alkyl, —$NH_2$, —NH—($C_1$–$C_4$-alkyl and —N(($C_1$–$C_4$-alkyl)$_2$;

$R_9$ is hydrogen, —CO—($C_1$–$C_4$)-alkyl, or ($C_1$–$C_7$)-alkyl, ($C_3$–$C_7$)-cycloalkyl, ($C_1$–$C_7$)-alkenyl or ($C_1$–$C_7$-alkynyl, each of which is optionally substituted with one, two or three groups selected from —OH, —O—($C_1$–$C_5$)-alkyl, —$NH_2$, —NH—($C_1$–$C_4$)-alkyl and —N(($C_1$–$C_4$-alkyl)$_2$;

$R_{10}$ $R_{11}$ and $R_{12}$ independently represent halogen, —OH, aryl, heteroaryl, —O—($C_1$–$C_{10}$)-alkyl, —O—($C_1$–$C_7$)-alkyl-$R_7$, —O-aryl, —O-heteroaryl, —SH, —S—($C_1$–$C_{10}$)-alkyl, —S—($C_1$–$C_7$)-alkyl-$R_7$, —S-aryl, —S-heteroaryl, —P(O)($C_1$–$C_5$)-alkyl)$_2$, —P(O)(OH)$_2$, —CN, —$NR_8R_9$, —CO—$NH_2$, —CO—NH—($C_1$–$C_3$)alkyl, —CO—N(($C_1$–$C_3$)alkyl)$_2$, —COOH —CO—O—($C_1$–$C_5$)-alkyl, heterocyclyl, or oxo;

n is 0, 1, or 2; and m is 2, 3, or 4.

5. A method for treating a tumor in a subject in need thereof, wherein the tumor is selected from the group consisting of sarcomas, carcinomas, and mesotheliomas, comprising administering to said subject a therapeutically effective amount of a compound having the formula:

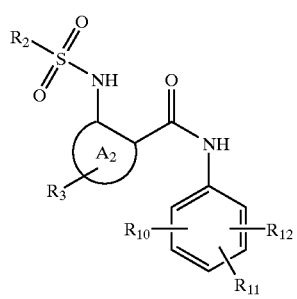

or a pharmaceutically acceptable salt, ester, or amide thereof wherein $A_2$ is phenyl;

$R_2$ is phenyl which may be optionally substituted with one, two or three groups selected from halogen, —OH, aryl, heteroaryl, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, —P(O)(O—)$(C_1-C_5)$-alkyl$)_2$, —P(O)(OH)$_2$, —CN, —$NR_8R_9$, —CO—$NH_2$, —CO—NH—$(C_1-C_3)$-alkyl, —CO—N(($C_1-C_3$)-alkyl)$_2$, —COOH, —CO—O—$(C_1-C_5)$-alkyl, heterocyclyl, and oxo;

$R_3$ is one, two or three substituents independently selected from hydrogen, halogen, —$CF_3$, —OH, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, $(C_1-C_3)$-alkylene dioxy, —CN, —$NO_2$, —$NR_8R_9$, —$CONR_5R_6$, —COOH, —CO—O—$(C_1-C_5)$-alkyl, heterocyclyl, —S(O)$_n$—$(C_1-C_7)$-alkyl, —S(O)$_n$-aryl, —S(O)$_n$-heteroaryl, —S(O)$_n$—$NR_5R_6$, or $(C_1-C_7)$-alkyl, $(C_3-C_7)$-cycloalkyl, $(C_1-C_7)$-alkenyl or $(C_1-C_7)$-alkynyl, each of which is optionally substituted with up to five groups independently selected from halogen, —OH, aryl, heteroaryl, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, —P(O)(O—$(C_1-C_5)$-alkyl)$_2$, —P(O)(OH)$_2$, —CN, —$NR_8R_9$, —CO—$NH_2$, —CO—NH—$(C_1-C_3)$-alkyl, —CO—N(($C_1-C_3$)-alkyl)$_2$, —COOH, —CO—O—$(C_1-C_5)$-alkyl, heterocyclyl, and oxo;

$R_5$ and $R_6$ independently are hydrogen, or $(C_1-C_{10})$-alkyl, $(C_3-C_{10})$-cycloalkyl, $(C_1-C_{10})$-alkenyl or $(C_1-C_{10})$-alkynyl, each of which is optionally substituted with one, two or three groups selected from aryl, heteroaryl, heterocyclyl, —CO—$(C_1-C_{10})$-alkyl, —CO-aryl, —CO-heteroaryl, —CO-heterocyclyl, —$SO_2$—$(C_1-C_{10})$-alkyl, —$SO_2$-aryl —$SO_2$-heteroaryl, or —$SO_2$-heterocyclyl; or $R_5$ and $R_6$ together with the nitrogen atom to which they are attached form a 5, 6, 7 or 8-membered carbocyclic ring up to two of which members are optionally hetero atoms selected front N, O, and S, the carbocyclic ring being optionally substituted with up to five groups selected from halogen, $(C_1-C_5)$-alkyl, $(C_3-C_6)$-cycloalkyl, $(C_1-C_5)$-alkenyl, $(C_1-C_5)$-alkynyl, $(C_1-C_3)$-hydroxyalkyl, $(C_1-C_3)$-alkyl-O—$(C_1-C_4)$-alkyl, aryl, heteroaryl, —$CF_3$, —OH, —O—$(C_1-C_7)$-alkyl, —O-aryl, —O-heteroaryl, —O—$(C_2-C_4)$-alkyl-O—$(C_1-C_7)$-alkyl, $(C_2-C_3)$-alkylenedioxy, —$NR_8R_9$, —CN, —CO—$NH_2$, —CO—NH—$(C_1-C_3)$-alkyl, —CO—N(($C_1-C_3$)-alkyl)$_2$, —COOH, —CO—O—$(C_1-C_5)$-alkyl, —CHO, CO—$(C_1-C_5)$alkyl, —S(O)$_n$—$(C_1-C_4)$-alkyl, —S(O)$_n$—$NH_2$, —S(O)$_n$—NH—$(C_1-C_3)$-alkyl, —S(O)$_n$—N(($C_1-C_3$)-alkyl)$_2$, oxo, —$(CH_2)_m$—$NH_2$, —$(CH_2)_m$—NH—$(C_1-C_4)$-alkyl or —$(CH_2)_m$—N(($C_1-C_4$)-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_7$ is —OH, —O—$(C_1-C_7)$-alkyl, —$NH_2$, —NH—$(C_1-C_4)$-alkyl, or
—N(($C_1-C_4$-alkyl)$_2$, wherein the two alkyl groups are optionally linked by a single bond and then, together with the nitrogen atom to which they are attached, form a 5, 6, 7 or 8-membered carbocyclic ring in which one member is optionally selected from O, S or $NR_5$;

$R_8$ is hydrogen, or
$(C_1-C_7)$-alkyl, $(C_3-C_7)$-cycloalkyl, $(C_1-C_7)$-alkenyl or $(C_1-C_7)$-alkynyl, each of which is optionally substituted with one, two or three groups selected from —OH, —O—$(C_1-C_5)$-alkyl, —$NH_2$, —NH—$(C_1-C_4)$-alkyl and —N(($C_1-C_4$-alkyl)$_2$;

$R_9$ is hydrogen, —CO—$(C_1-C_4)$-alkyl, or
$(C_1-C_7)$-alkyl, $(C_3-C_7)$-cycloalkyl, $(C_1-C_7)$-alkenyl or $(C_1-C_7)$-alkynyl, each of which is optionally substituted with one, two or three groups selected from —OH, —O—$(C_1-C_5)$-alkyl, —$NH_2$, —NH—$(C_1-C_4)$-alkyl and —N(($C_1-C_4$-alkyl)$_2$;

$R_{10}$ $R_{11}$ and $R_{12}$ independently represent halogen, —OH, aryl, heteroaryl, —O—$(C_1-C_{10})$-alkyl, —O—$(C_1-C_7)$-alkyl-$R_7$, —O-aryl, —O-heteroaryl, —SH, —S—$(C_1-C_{10})$-alkyl, —S—$(C_1-C_7)$-alkyl-$R_7$, —S-aryl, —S-heteroaryl, —P(O)($C_1-C_5$-alkyl)$_2$, —P(O)(OH)$_2$, —CN, —$NR_8R_9$, —CO—$NH_2$, —CO—NH—$(C_1-C_3)$alkyl, —CO—N(($C_1-C_3$) alkyl)$_2$, —COOH, —CO—O—$(C_1-C_5)$-alkyl heterocyclyl, or oxo;

n is 0, 1, or 2; and m is 2, 3, or 4.

6. The method according to claim 1 wherein the compound is selected from 5-chloro-2-{[(4-chlorophenyl) sulfonyl]amino}-N-(4-chlorophenyl)benzamide; 5-bromo-2-{[(4-chlorophenyl)sulfonyl]amino}-N-(4-chlorophenyl) benzamide; (5-bromo-2-{[(4-chloro-3-nitrophenyl)sulfonyl] amino}phenyl)-N-(4-chlorophenyl)carboxamide; and N-(3, 4-dichlorophenyl)(5-chloro-2-{[(4-chlorophenyl)sulfonyl] amino}phenyl)carboxamide.

7. The method of claim 1 wherein the tumor is a sarcoma.
8. The method of claim 2 wherein the tumor is a sarcoma.
9. The method of claim 3 wherein the tumor is a sarcoma.
10. The method of claim 4 wherein the tumor is a sarcoma.
11. The method of claim 5 wherein the tumor is a sarcoma.
12. The method of claim 6 wherein the tumor is a sarcoma.
13. The method according to claim 1 wherein the compound is 5-chloro-2-{[(4-chlorophenyl)sulfonyl]amino}-N-(4-chlorophenyl)benzamide.
14. The method of claim 7 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

15. The method of claim 8 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

16. The method of claim 9 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

17. The method of claim 10 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

18. The method of claim 11 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

19. The method of claim 12 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

20. The method of claim 1 wherein the tumor is a carcinoma.

21. The method of claim 2 wherein the tumor is a carcinoma.

22. The method of claim 3 wherein the tumor is a carcinoma.

23. The method of claim 4 wherein the tumor is a carcinoma.

24. The method of claim 5 wherein the tumor is a carcinoma.

25. The method of claim 6 wherein the tumor is a carcinoma.

26. The method of claim 20 wherein the carcinoma is an ovarian carcinoma.

27. The method of claim 21 wherein the carcinoma is an ovarian carcinoma.

28. The method of claim 22 wherein the carcinoma is an ovarian carcinoma.

29. The method of claim 23 wherein the carcinoma is an ovarian carcinoma.

30. The method of claim 24 wherein the carcinoma is an ovarian carcinoma.

31. The method of claim 25 wherein the carcinoma is an ovarian carcinoma.

32. The method of claim 1 wherein the tumor is a mesothelioma.

33. The method of claim 2 wherein the tumor is a mesothelioma.

34. The method of claim 3 wherein the tumor is a mesothelioma.

35. The method of claim 4 wherein the tumor is a mesothelioma.

36. The method of claim 5 wherein the tumor is a mesothelioma.

37. The method of claim 6 wherein the tumor is a mesothelioma.

38. The method of claim 32 wherein the mesothelioma is a lung mesothelioma.

39. The method of claim 33 wherein the mesothelioma is a lung mesothelioma.

40. The method of claim 34 wherein the mesothelioma is a lung mesothelioma.

41. The method of claim 35 wherein the mesothelioma is a lung mesothelioma.

42. The method of claim 36 wherein the mesothelioma is a lung mesothelioma.

43. The method of claim 37 wherein the mesothelioma is a lung mesothelioma.

44. The method of claim 13 wherein the tumor is a sarcoma.

45. The method of claim 44 wherein the sarcoma is selected from the group consisting of stromal cell sarcomas, leiomyosarcomas, malignant fibrous histiocytomas, Ewing sarcomas, fibrosarcomas, chondrosarcomas, osteosarcomas, liposarcomas, rhabdomyo-sarcomas, hemangiocytomas, and myxosarcomas.

46. The method of claim 13 wherein the tumor is a carcinoma.

47. The method of claim 46 wherein the carcinoma is an ovarian carcinoma.

48. The method of claim 13 wherein the tumor is a mesothelioma.

49. The method of claim 48 wherein the mesothelioma is a lung mesothelioma.

* * * * *